United States Patent [19]

Proctor et al.

[11] Patent Number: 4,538,623
[45] Date of Patent: Sep. 3, 1985

[54] THREAD ELECTRODE ASSEMBLY

[75] Inventors: Keith J. Proctor, Fridley; John D. Doring, Spring Lake Park, both of Minn.

[73] Assignee: Medtronic, Inc., Minneapolis, Minn.

[21] Appl. No.: 597,953

[22] Filed: Apr. 9, 1984

[51] Int. Cl.³ ............................................. A61N 1/04
[52] U.S. Cl. .................................................. 128/784
[58] Field of Search ............ 128/419 P, 642, 784–786; 339/79

[56] References Cited

U.S. PATENT DOCUMENTS 1,584,533  5/1926  Hands ..................................... 339/67
4,444,206  4/1984  Gold ................................. 128/419 P
4,463,765  8/1984  Gold ..................................... 128/785

Primary Examiner—William E. Kamm
Attorney, Agent, or Firm—John L. Rooney; Joseph F. Breimayer; Reed A. Duthler

[57] ABSTRACT

A threaded pacing electrode assembly for use in implantable electrical leads. The electrode is provided with an exposed portion adapted to make electrical contact with body tissue and with a cylindrical portion proximal to the exposed portion provided with a helical screw thread. A conductor coil which has an inner diameter smaller than the outer diameter of the cylindrical portion is mounted to the exterior of the cylindrical portion, coiled within the screw thread. A transparent insulating sleeve covers the cylindrical portion, is frictionally retained by the thread, and assists in maintaining the conductor coils in contact with the cylindrical portion.

6 Claims, 3 Drawing Figures

U.S. Patent  Sep. 3, 1985  4,538,623
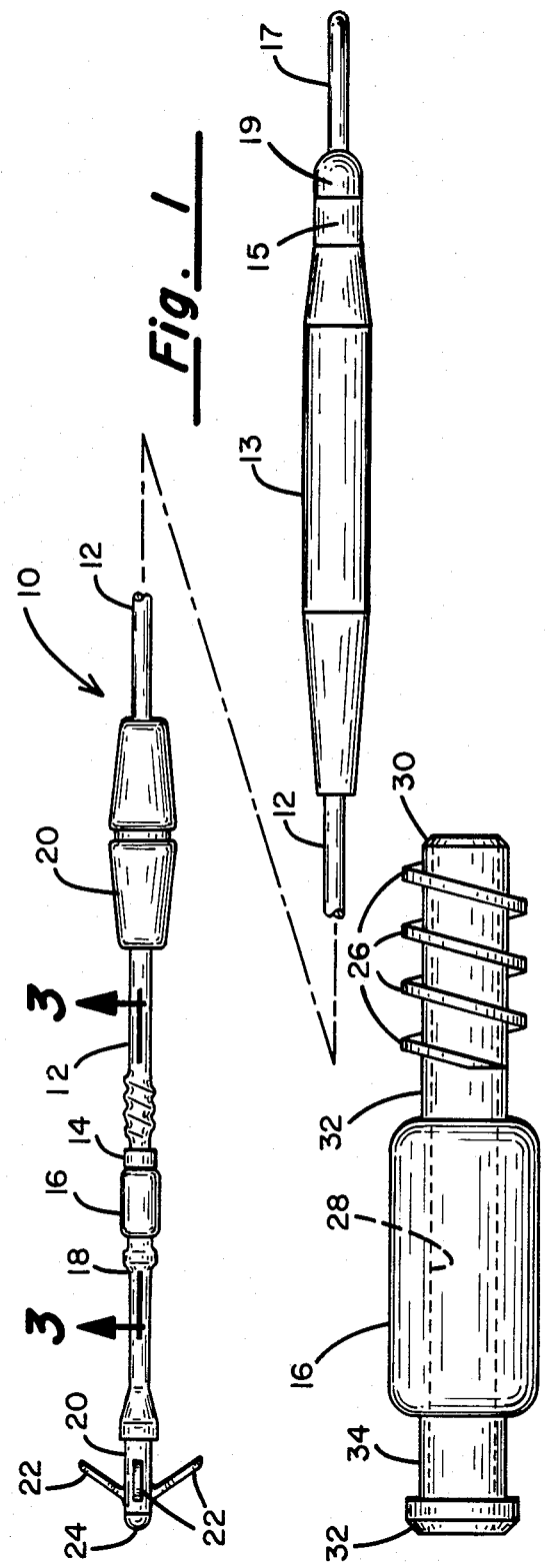
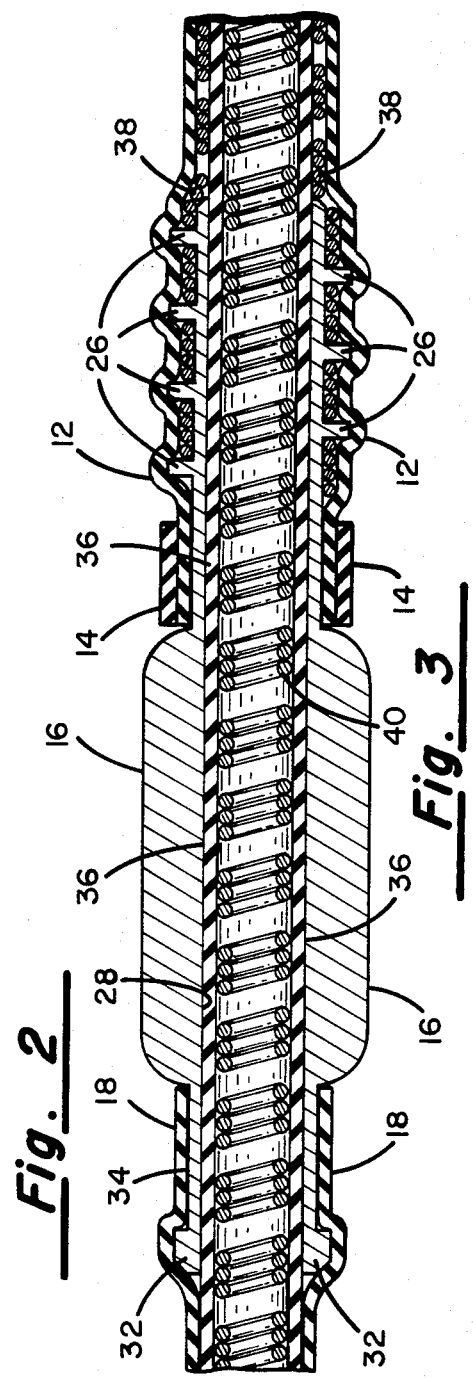

THREAD ELECTRODE ASSEMBLY

BACKGROUND OF THE INVENTION

The present invention relates generally to medical electrical leads, and more particularly to electrode assemblies for use on medical electrical leads.

Previously known electrodes for use with medical electrical leads have generally been connected to the conductor of the electrical lead by means of a weld, as illustrated in U.S. Pat. No. 3,348,548 by means of a crimp as illustrated in U.S. Pat. No. 4,338,947 or by means of a swaging core as illustrated in U.S. Pat. No. 4,328,812. Adhesive attachment has also been used, as shown in U.S. Pat. No. 3,568,660. The use of welds to attach electrodes to medical electrical leads has generally fallen out of favor, due to the high temperatures required to effect the weld, and due to the difficulty of sealing the lead around the weld. More popular are the crimped and swaged electrodes. However, the crimping and swaging methods of attachment, as illustrated in the above cited patents, have the inherent disadvantage that the connection is made inside the electrode structure. As a result, the integrity of the attachment cannot be inspected visually. Because these electrodes typically employ metals which are not easily penetrated by x-rays, a number of sample assemblies must be tested destructively to mechanically determine the strength of the attachments.

SUMMARY OF THE INVENTION

The present invention provides a novel electrode structure which provides a secure attachment of an electrode to a coiled conductor which can be inspected visually. The coupling of the coil to the electrode is accomplished by screwing the conductor coil on to a threaded cylindrical portion of the electrode so that the coils of the conductor lie between the coils of the thread. The outer diameter of the cylindrical portion is slightly larger than the inner diameter of the conductor coil when relaxed so that the elasticity of the conductor coil holds it tightly around the cylindrical portion. In order to remove the coil, it is necessary to unscrew it from the thread. However, torque applied to the coil conductor proximal to the electrode that would tend to unscrew the coil from the threaded section would also tend to further tighten the coil around the cylindrical portion, preventing its removal.

The thread of the cylindrical portion extends further radially from the electrode assembly than the conductor coils lying within the thread. This feature, when combined with an elastic outer insulating sleeve having a relaxed inner diameter less than that of the conductor coil as mounted on the threaded section, results in the insulative sheath being frictionally retained by the thread, and allows the insulative sheath to urge the conductor coil into firmer contact with the cylindrical portion intermediate the coils of the thread. Use of a transparent insulative sheath, such as polyurethane or clear silicone rubber, allows the entire assembly to be visually inspected. If a defect is discovered, the parts may be disassembled and one or more of the parts may be reused. The invention thus provides a distinct advantage in comparison with the swaging and crimping methods, which are essentially irreversible, requiring the scrapping of the entire structure upon detection of a defect in the assembly. Sealing the insulative sheath to the electrode is accomplished by the use of an elastic band, holding the sheath in contact with the cylindrical portion distal to the thread.

An additional advantage of the present invention is that the absence of a swaging core allows the electrode to be provided with an inner bore, equal in diameter to the inner diameter of the conductor coil. This provides a smooth passage way of constant diameter for a second conductor coil or for a stylet. This structure is believed advantageous in reducing problems of the stylet snagging or sticking at the electrode assembly, found in some prior art swaged and crimped electrode assemblies.

BRIEF DESCRIPTION OF THE DRAWINGS

FIG. 1 illustrates a side plan view of a lead employing the threaded electrode assembly of the present invention.

FIG. 2 illustrates a side plan view of the electrode of the present invention, displaying the exposed portion, as well as the cylindrical portion.

FIG. 3 shows a cross sectional view of the lead of FIG. 1, at the point of the electrode assembly, showing the interrelationship of all portions of the assembly.

DETAILED DESCRIPTION OF THE PREFERRED EMBODIMENT

FIG. 1 shows a side plan view of a pacing lead incorporating the threaded electrode of the present invention. At the distal end of the lead is located an electrode 24, mounted within a urethane sheath 20 which bears four tines 22. The structure of the electrode and the associated tines are more fully set forth in U.S. Pat. No. 3,902,501 issued to Citron et al and incorporated herein by reference.

Extending from insulative sheath 20 to the electrode assembly is insulative sheath 18, which is seen mounted external to the proximal end of electrode 16. Proximal to the exposed portion of electrode 16 is elastic ring 14 which tightly holds insulative sheath 12 to the electrode. The threads of the electrode assembly are visible through transparent, insulative sheath 12. At the proximal end of the lead is connector assembly 13, which is provided with a first electrical connector 15, electrically coupled to electrode 16 and with a second electrical connector 17, electrically coupled to tip electrode 24. Intermediate connectors 15 and 17 is insulative segment 19.

FIG. 2 shows a side sectional view of electrode 16. The distal portion of the electrode is provided with a cylindrical segment 34, bearing a chamferred flange 33. The proximal portion of the electrode comprises a cylindrical portion 32 which bears a screw thread 26 which spirals around cylindrical portion 32. Running from the proximal end to the distal end of electrode 16 is bore 28. At the proximal end of the electrode, bevel 30 extends from the outer diameter of cylindrical portion 32 to inner bore 28.

FIG. 3 illustrates in cross section the electrode assembly as used in a bipolar medical electrical lead. Electrode 16 is preferably machined out of a conductive, inert metal such as platinum, titanium or stainless steel. In this view, it is seen that the inner diameter of bore 28 of electrode 16 is equal to the inner diameter of conductor coil 38 in its relaxed state. Conductor coil 38 is a quadrifilar coil, preferably manufactured of drawn-brazed strand wire or of MP35N alloy. While it is not necessary to the invention that conductor 38 be quadrifilar, it is desirable, as will be discussed below. The pitch of the coils of conductor 38 is equal to the pitch of thread 26.

Conductor coil 38 is shown encircling cylindrical portion 32 of electrode 16. Because the outer diameter of cylindrical segment 32 is larger than the inner diameter of coil 38 in its relaxed state, coil 38 holds itself snuggly against the outer surface of cylindrical portion 32. Screw thread 26 is seen to extend radially from conductor coil 38. Transparent insulative sheath 12 in its relaxed state takes the form of an elongated tube having an inner diameter approximately equal to the outer diameter of conductor coil 38, in its relaxed state. Insulative sheath 12 encircles and covers cylindrical portion 32 of electrode 16. Because insulative sheath 38 is made of an elastic material, such as polyurethane, it tends to return to its original diameter in areas between the coils of thread 26. As such, sheath 12 further assists in urging coil 38 against the electrode. The fact that coil 38 is quadrifilar assists in this process by providing an area of sufficient width to allow sheath 12 to contract into contact with coil 38. The contraction of insulative sheath 12 also assists thread 26 in holding sheath 12 in frictional engagement to the electrode. A fluid seal of sheath 12 to cylindrical portion 32 of the electrode 16 is provided by an elastic band 14 which tightly holds the sheath and electrode in contact with one another.

Interior to bore 28 of electrode 16 is located conductor coil 40, surrounded by insulative sheath 36. Because the inner diameter of bore 28 is equal to the inner diameter of conductor 38, there are no abrupt transitions of diameter. This fact provides the structure through which a stylet may easily be passed. In addition, because no crimping or swaging steps have been used to produce the electrode, neither electrode 16 nor inner coil 40 has been subjected to any deforming stress, so that bore 28 remains circular, reducing the chances of sticking or snagging of a stylet when passed through the electrode assembly.

At the distal end of electrode 16 is located a second cylindrical section 34, provided with a bevelled flange 33. Bevelled flange 33 serves as a means of attachment of insulative sheath 18, which encircles inner insulative sheath 36.

The above described embodiment sets forth a ring electrode. However, the invention is equally applicable to a tip electrode, or other electrode configurations.

What is claimed is:
1. An electrode lead comprising:
    a coiled conductor having a proximal end and a distal end;
    a tubular insulative sheath having a proximal end, a distal end, and a central lumen in which said coiled conductor is located; and
    an electrode mounted to the distal end of said insulative sheath and having a distal portion exposed to the exterior of said insulative sheath and a cylindrical portion proximal to said distal portion, located within the lumen of said insulative sheath, wherein said cylindrical portion of said electrode is provided with a helical screw thread and said coiled conductor is mounted around said cylindrical portion, the coils of said coiled conductor lying between the coils of said helical screw thread, the threads of said helical screw thread extending radially beyond the coils of said coiled conductor and said cylindrical portion of said electrode having an outer diameter greater than the inner diameter of said coiled conductor in its relaxed state.

2. An electrode lead according to claim 1 wherein said tubular insulative sheath is elastic and wherein the inner diameter of the lumen of said tubular insulative sheath, in its relaxed state, is less than the outer diameter of said helical screw thread.

3. An electrode lead according to claim 2 wherein the diameter of the lumen of said insulative sheath, in its relaxed state, is less than the outer diameter of the coils of said coiled conductor, lying between the threads of said helical screw thread.

4. An electrode according to claim 3, further comprising an elastic band, located proximal to said distal portion of said electrode, encircling the distal end of said insulative sheath distal to said helical screw thread, sealing said insulative sheath to the cylindrical portion of said electrode.

5. A lead according to claim 1 wherein said electrode has a longitudinal lumen having an inner diameter equal to the inner diameter of said coiled conductor in its relaxed state.

6. An electrode lead according to claim 5 wherein said cylindrical portion of said electrode is provided with a bevel extending from the exterior of said cylindrical portion to the lumen of said electrode.

* * * * *